United States Patent [19]
Miyagi et al.

[11] Patent Number: 5,636,625
[45] Date of Patent: Jun. 10, 1997

[54] TRACHEAL AIRWAY APPARATUS

[75] Inventors: Kunihiko Miyagi; Masahiro Inoue, both of Saitama-ken, Japan

[73] Assignee: Machida Endoscope Co., Ltd., Tokyo, Japan

[21] Appl. No.: 514,097

[22] Filed: Aug. 11, 1995

[30] Foreign Application Priority Data

Aug. 30, 1994 [JP] Japan .................................. 6-228753

[51] Int. Cl.⁶ .................................................. A61M 16/00
[52] U.S. Cl. ............................... 128/200.26; 128/207.14
[58] Field of Search ................................ 600/125, 136; 128/200.26, 207.14, 207.15

[56] References Cited

U.S. PATENT DOCUMENTS

| | | | |
|---|---|---|---|
| 4,561,446 | 12/1985 | Hetz | 128/660 |
| 4,846,153 | 7/1989 | Berci | 128/200.26 |
| 4,878,485 | 11/1989 | Adair | 600/125 |
| 5,154,164 | 10/1992 | Chikama | 600/125 |
| 5,159,919 | 11/1992 | Chikama | 600/125 |
| 5,201,908 | 4/1993 | Jones | 600/125 |
| 5,257,617 | 11/1993 | Takahashi | 600/125 |
| 5,329,940 | 7/1994 | Adair | 128/200.26 |
| 5,413,092 | 5/1995 | Williams, III et al. | 600/125 |

FOREIGN PATENT DOCUMENTS

| | | |
|---|---|---|
| 280384 | 8/1988 | European Pat. Off. |
| 6-217933 | 8/1994 | Japan |
| WO-A-91 12044 | 8/1991 | WIPO |

Primary Examiner—Aaron J. Lewis
Attorney, Agent, or Firm—Fish & Richardson, P.C.

[57] ABSTRACT

A tracheal airway apparatus includes an insert tube and an endoscope. The endoscope includes a body and an insert portion extending forwardly of the body and inserted into the insert tube. The insert portion is of a double tubular structure. An inner tube of the insert portion is flexible and receives an illumination light transmission element and an image transmission element. An outer tube of the insert portion has a semi-hard property and is detachably attached to a front end part of the body. A space is formed between an inner periphery of the outer tube and an outer periphery of the inner tube.

13 Claims, 8 Drawing Sheets

TRACHEAL AIRWAY APPARATUS

BACKGROUND OF THE INVENTION

This invention relates to an apparatus for ensuring that the tracheal airway remains open, when a person suffers damage at the tracheal airway area or in other similar cases.

When a person is badly damaged in the throat area by traffic accident or the like, that person frequently has a difficulty in breathing and it sometimes endangers the life of the person. For this reason, at the site of the accident, it is extremely urgent to ensure that the airway remains open. A typical conventional apparatus for ensuring an open airway comprises an insert tube and a stylet. The stylet is formed, for example, of an aluminum core covered with a synthetic resin material so that it has a semi-hard property. Owing to this feature, the stylet can be manually bent and this bending contour of the stylet can be maintained without allowing its returning to the original contour due to its resiliency. The operator inserts the bent stylet, which is already received in the insertion tube, into the airway from the mouth of the patient (person who met the traffic accident, etc.) while observing the airway through a throat mirror at a position away from the patient. After the stylet has been fully inserted into the airway, only the stylet is withdrawn leaving the insert tube in the airway, and oxygen is supplied to the patient's lungs through the insert tube. The above-mentioned apparatus is sometimes used for other purposes than in the case of a damaged airway, such as oxygen inhalation and anesthetic gas inhalation.

In the tracheal airway apparatus thus constructed, much difficulty is often encountered in inserting the insert tube with the stylet received therein into the patient's airway because the airway cannot be seen clearly through the throat mirror despite an effort to open the patient's mouth widely. Therefore, only a well trained expert can become an operator of this type of an apparatus.

Japanese Laid-Open Patent Application No. Hei 6-217933 discloses a technique for inserting an insert tube with a flexible insert portion of an endoscope received therein into the airway while observing the airway through the endoscope. However, since the insert portion of the endoscope is flexible, it is difficult to insert the insert portion of the endoscope and insert tube smoothly into the airway particularly when the patient's throat area is damaged.

The above-mentioned Japanese Laid-Open Patent Application No. Hei 6-217933 also discloses an improved tracheal airway apparatus. As best seen in FIG. 3 of the above publication, the tracheal airway apparatus includes an endoscope and a stylet. The endoscope includes a body and a flexible insert portion extending from the body. A guide channel is formed in the endoscope. The guide channel has an inlet port opening to the body and an outlet port opening to a distal end face of the insert portion. In a state where the stylet is inserted into the guide channel, the insert portion is bent so as to be easily inserted into the airway. This bent form or contour of the insert portion is maintained by the stylet. With this bent contour, the insert portion of the endoscope is inserted into the airway while observing the airway. Thereafter, the stylet is withdrawn from the guide channel and a gas such as oxygen is supplied through the guide channel. As apparent from the description so far made, the endoscope is used as an insert tube in a general tracheal airway apparatus. However, a sectional flow area of the guide channel used for supplying a gas is small. Further, the stylet is formed to have a thin design in order to be smoothly inserted into the guide channel. Since the contour maintaining ability of the stylet is decreased, much difficulty is encountered when the insert portion of the endoscope is inserted into the airway particularly in the case where the patient's throat area is damaged.

SUMMARY OF THE INVENTION

It is, therefore, an object of the present invention to provide a tracheal airway apparatus which can be easily inserted into the airway and in which gas can be supplied in a stable manner.

According to the present invention, there is provided a tracheal airway apparatus comprising:

(a) an insert tube to be inserted into a tracheal airway;

(b) an endoscope including a body and an insert portion extending forwardly of the body and inserted into the insert tube; and (c) the insert portion of the endoscope including an outer tube and an inner tube received in the outer tube, the inner tube being flexible and receiving illumination light transmission means and image transmission means, the outer tube having a semi-hard property, a rear end of the outer tube being detachably attached to a distal end part of the body through connection means.

DETAILED DESCRIPTION OF THE EMBODIMENT

One embodiment of a tracheal airway apparatus will now be described with reference to FIGS. 1 to 7.

Figure 1:
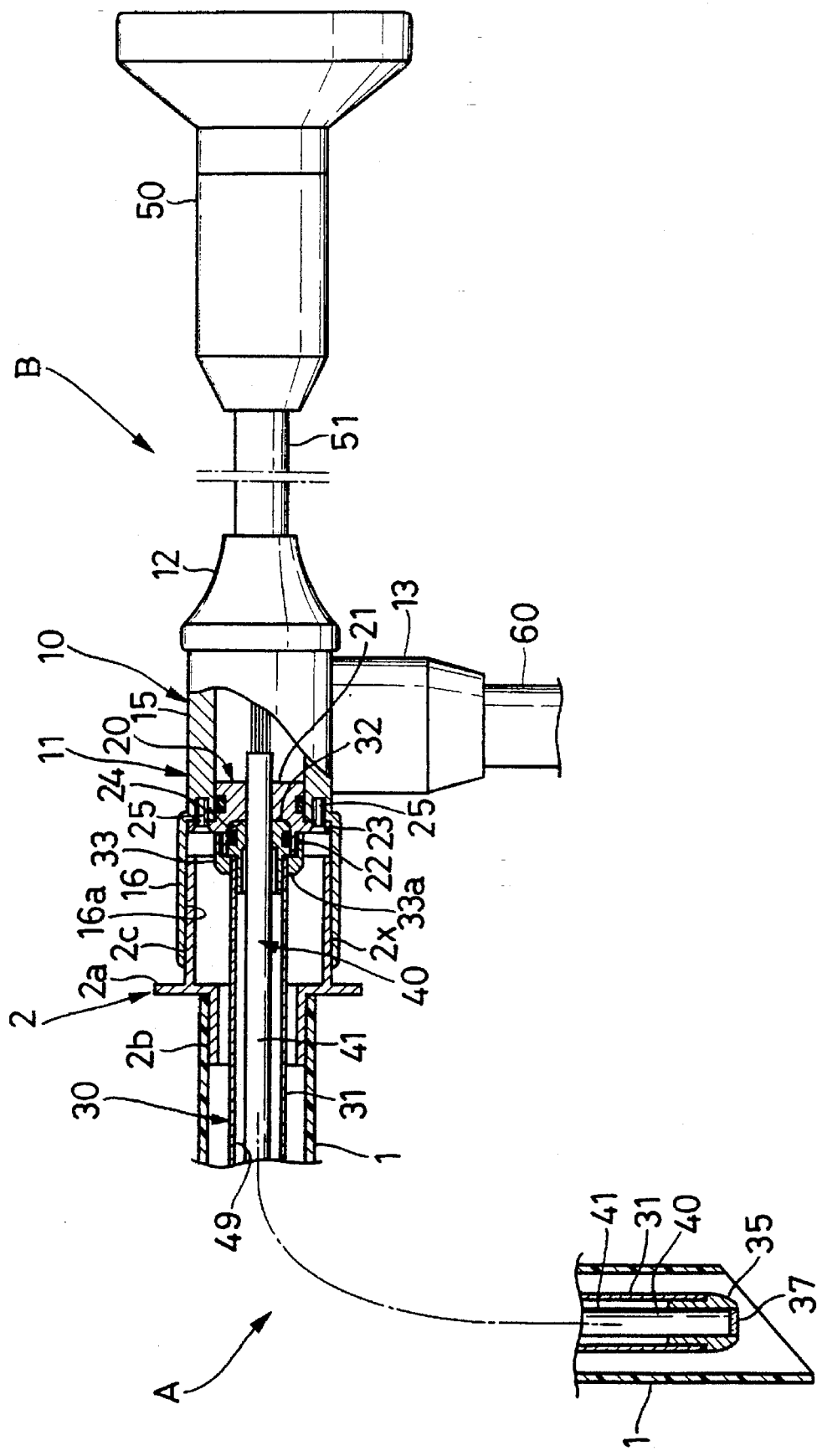
FIG. 1 is a side view, partly in section, of a tracheal airway apparatus according to one embodiment of the present invention.

As shown in FIG. 1, the tracheal airway apparatus includes an insert tube structure A to be inserted into a tracheal airway of a patient and an endoscope B for visually observing the inner wall of the tracheal airway when the insert tube structure A is inserted into the tracheal airway.

Figure 3:
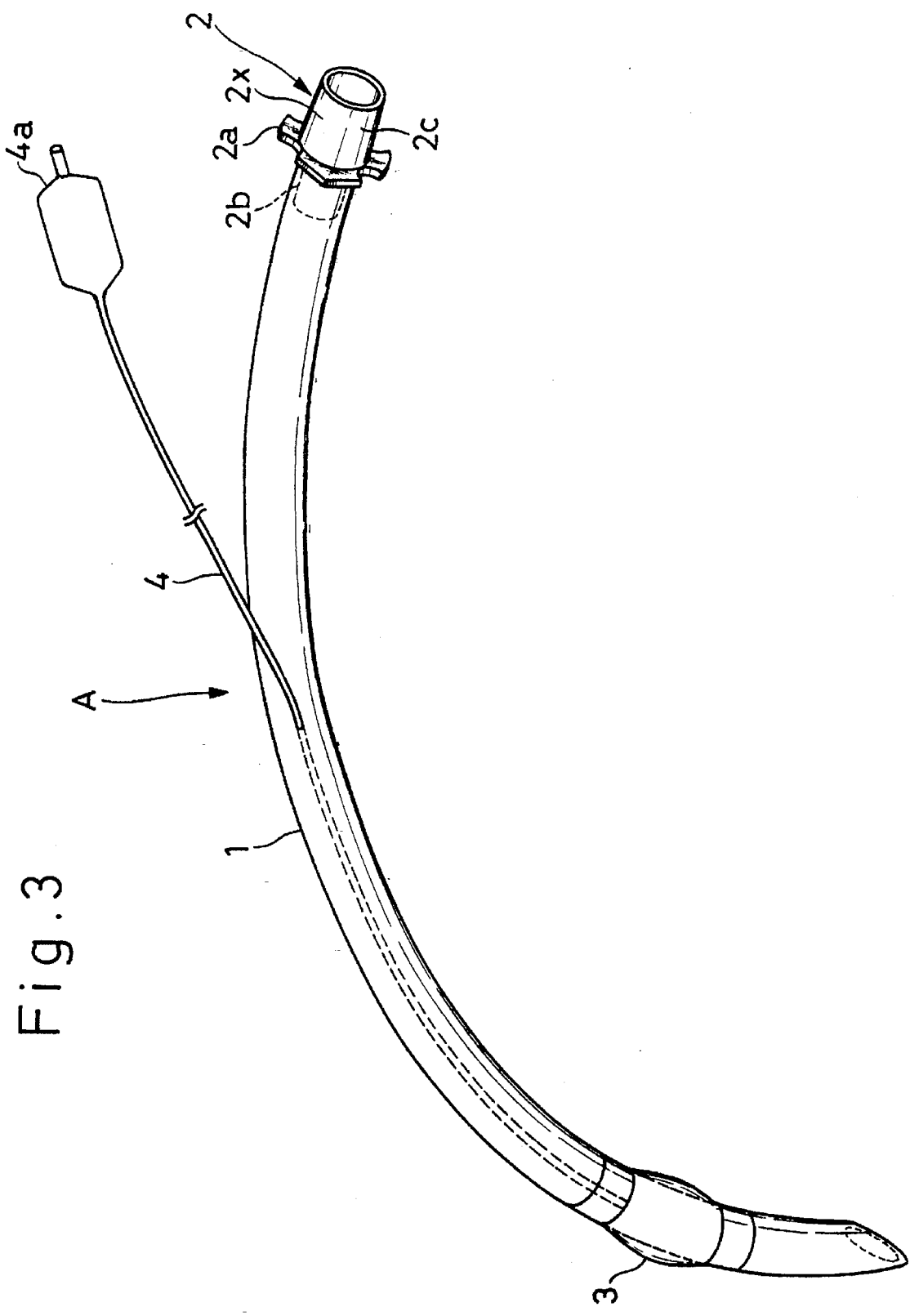
FIG. 3 is a perspective view of an insert tube structure used in the apparatus of FIG. 1.
Figure 4:
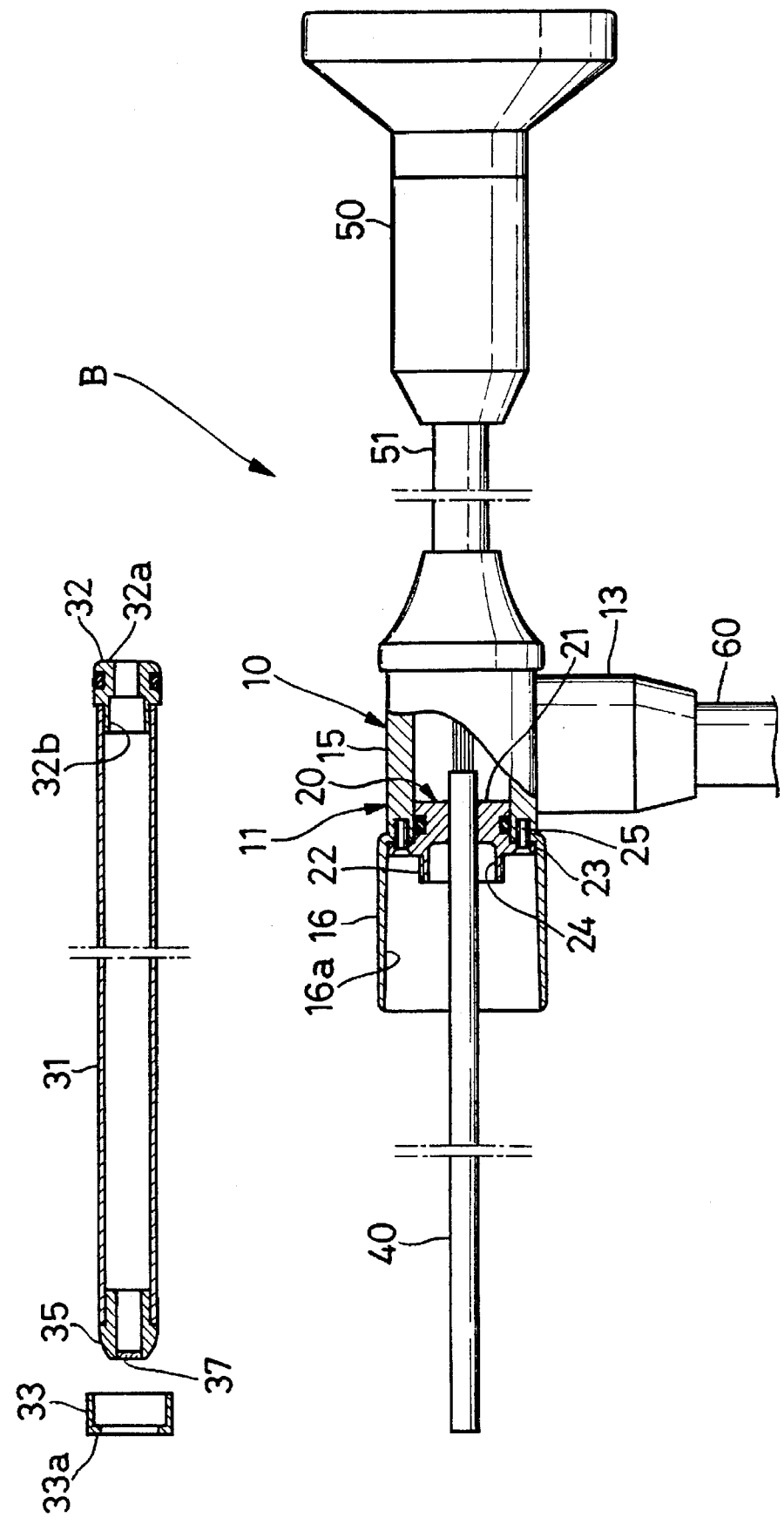
FIG. 4 is a side view, partly in section, of the endoscope in a state where a sheath is separated therefrom.

First, the insert tube structure A will be described. As is best seen in FIG. 3, the insert tube structure A includes a tube 1 molded of a synthetic resin, an attachment 2 fixedly secured to a rear end of the tube 1, and a balloon 3 fixed to the tube 1 in the vicinity of a distal end part of the same. The tube 1 exhibits a curved contour and has such low rigidity that it is readily transformed when a certain intensity of force is applied to the tube 1. The distal end of the tube 1 is slantwise cut off so as to allow the tube 1 to be easily inserted into the tracheal airway. The attachment 2 includes a flange 2a, a first sleeve portion 2b located forwardly of the flange 2a, and a second sleeve portion 2c located rearwardly of the flange 2a and having an outer diameter larger than that of the first sleeve portion 2b. The first sleeve portion 2b is press-fitted into a rear end part of the tube 1 so that it is fixed to the tube 1. The second tube portion 2c is coaxial with the first sleeve portion 2b and served as a rear end part of the insert tube structure A. An outer surface of the second sleeve portion 2c is a tapered surface 2x whose outer diameter is increasingly enlarged toward the distal end part of the tube 1. Opposite ends of the balloon 3 are adhesively secured to an outer peripheral surface of the tube 1 but an intermediate part of the balloon 3 is not adhesively secured to the same. A foremost end of a fine tube 4 extending through a peripheral wall of the tube 1 is connected to the balloon 3. The fine tube 4 extends along an inner surface of the tube 1 in the rearward direction, extends through the peripheral wall of the tube 1 at an intermediate part of the same, and then, extends further in the rearward direction. A compressed air receiving portion 4a is disposed at a rear end of the fine tube 4. A compressed air fed to the receiving portion 4a is allowed to flow through the fine tube 4 and supplied to a space between an intermediate part of the balloon 3 and the outer peripheral surface of the tube 1. This causes the balloon 3 to expand.

Figure 2:
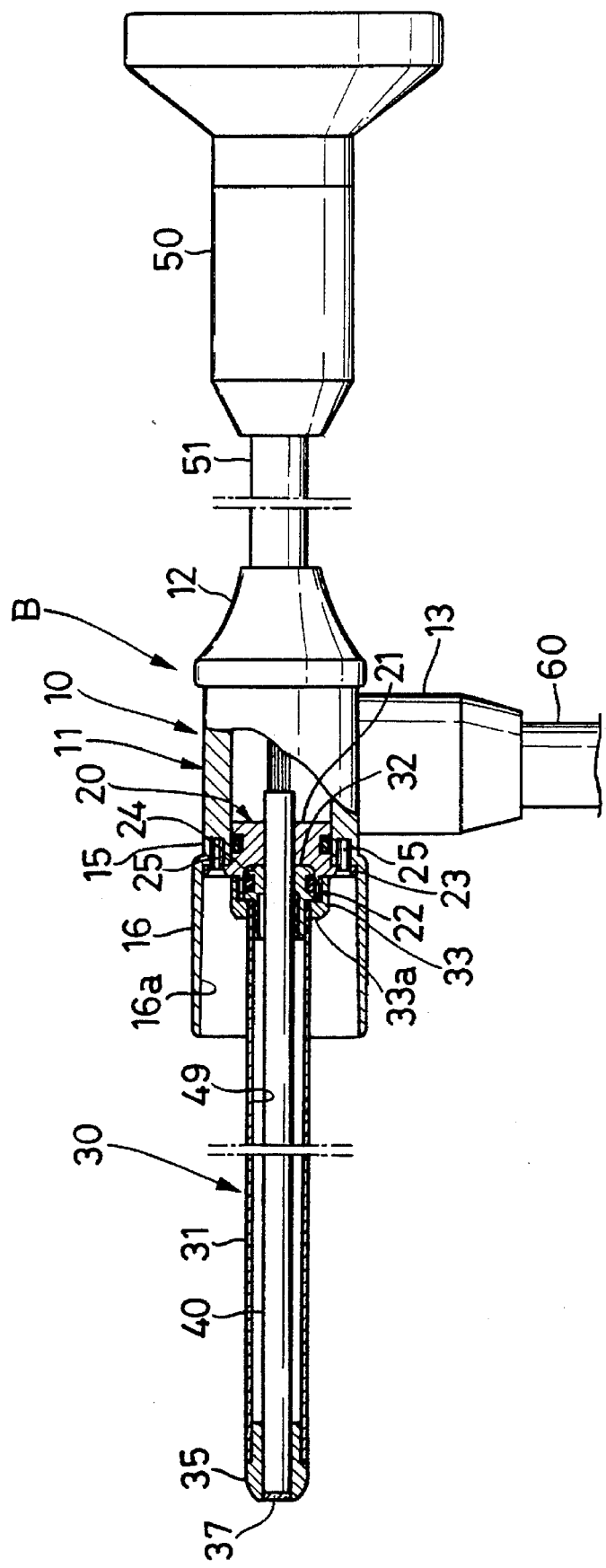
FIG. 2 is a side view, partly in section, of an endoscope used in the apparatus of FIG. 1.

Next, the endoscope B will be described in detail. As shown in FIGS. 1 and 2, the endoscope B includes a body 10, an insertion portion 30 extending forwardly of the body 10, and an eye piece portion 50 disposed rearwardly of the body 10.

The body 10 includes a first sleeve 11, a second sleeve 12 coaxially connected to a rear end of the first sleeve 11, a third sleeve 13 connected to a peripheral wall of the first sleeve 11 with the axial lines of the first and third sleeves 11 and 13 perpendicularly intersected each other, and an attachment 20 (a front wall of the body 10) fixedly received at an intermediate portion in the axial direction of the first sleeve 11. A distal end of a semi-hard tube 51 is fixedly secured to the second sleeve 12, and the eye piece portion 50 is disposed at a rear end of the tube 51. One end of a flexible light guide tube 60 is connected to the third sleeve 13. An optical connector is connected to the other end of the light guide tube 60.

Figure 5:
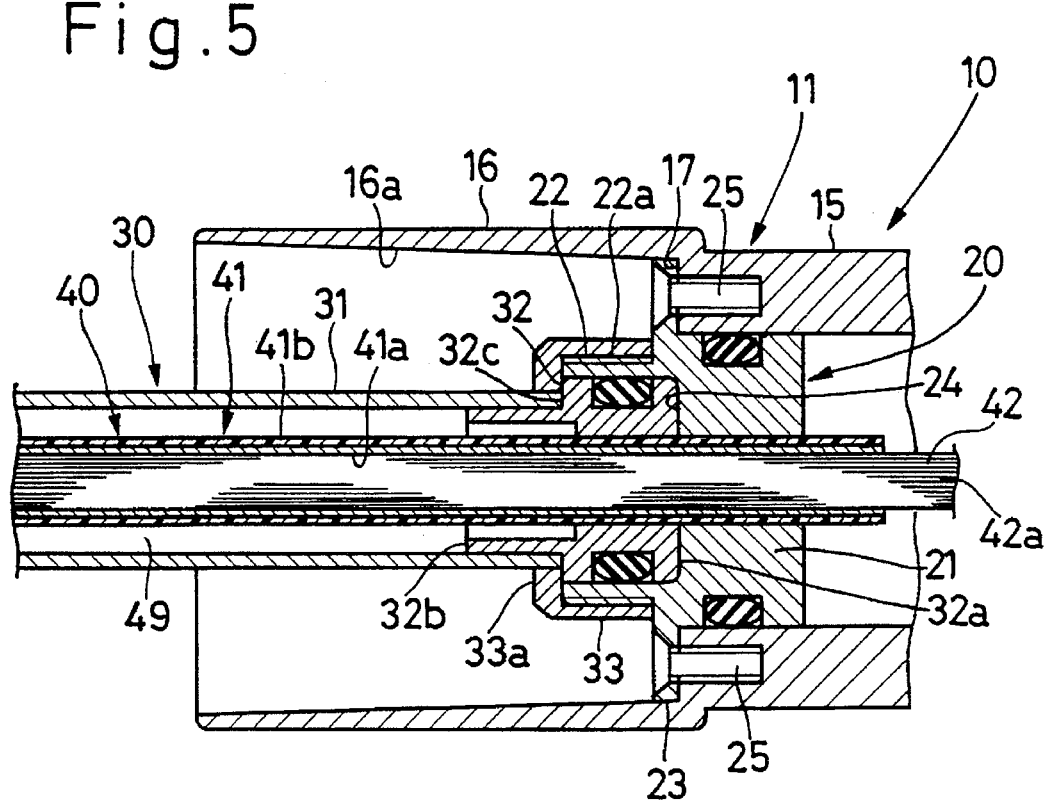
FIG. 5 is an enlarged sectional view showing a front part of a body of the endoscope and a rear end part of an insert portion.

As is best seen in FIG. 5, the first sleeve 11 exhibits a cylindrical contour and includes a base sleeve portion 15 at a rear part thereof and a fitting sleeve portion 16 at a fore part thereof. The fitting sleeve portion 16 is served to allow the insert tube structure A to be detachably fitted thereto, and an inner diameter of the fitting sleeve portion 16 is dimensioned to be larger than that of the base sleeve portion 15 with a stepped part 17 (FIG. 5) formed therebetween. An inner peripheral surface of the fitting sleeve portion 16 is a tapered surface 16a whose inner diameter is increasingly enlarged toward a distal end of the fitting sleeve portion 16. A tapered angle of the tapered surface 16a is equal to that of the tapered surface 2x of the second sleeve portion 2c of the insert tube structure A.

As shown in FIG. 5, the attachment 20 of the body 10 includes a cylindrical base portion 21 having a heavy thickness at a rear part thereof, a receiving portion 22 having a small thickness and an outer diameter smaller than that of the base portion 21 at a fore part thereof, and a flange portion 23 outwardly extending in the radial direction at the intermediate part thereof. The base portion 21 of the attachment 20 is received in the base sleeve portion 15 of the first sleeve 11, and the flange portion 23 fixedly secured to the stepped part 15 by tightening a plurality of screws 25 while coming in contact with the stepped part 17 of the first sleeve 11. The receiving portion 22 is served to receive a rear end part of a sheath 31 of an insert portion 30 to be described later and coaxially disposed inside of the fitting sleeve portion 16 of the first sleeve 11. A threaded portion 22a is formed on an outer peripheral surface of the receiving portion 22. A receiving cavity 24 for receiving an attachment 32 of a sheath 31 to be described later is formed on a front surface of the attachment 22, and the receiving cavity 24 is surrounded by the receiving portion 22.

Figure 7:
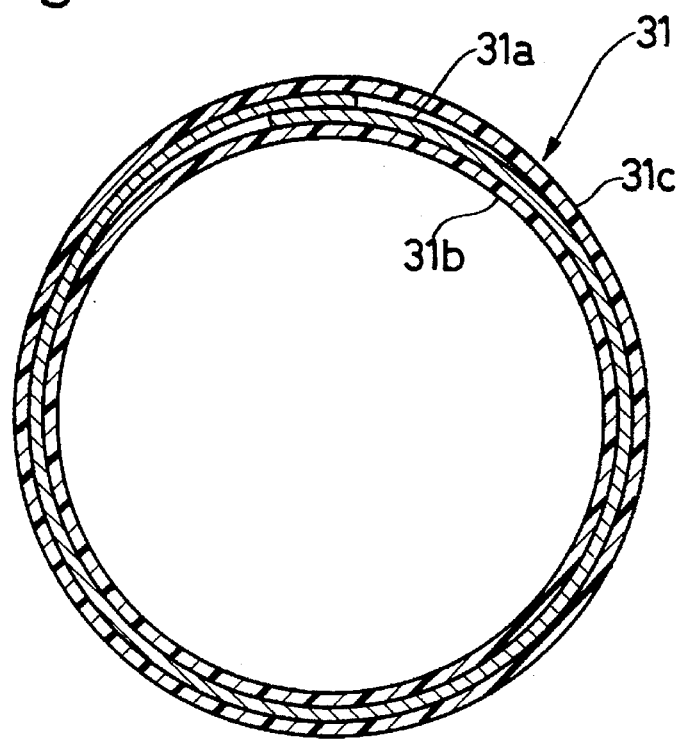
FIG. 7 is an enlarged sectional view of the sheath.

As shown in FIGS. 1 and 2, the insert portion 30 of the endoscope B includes the elongated cylindrical semi-hard sheath 31 (outer tube), and an elongated content 40 received in the sheath 31. As is shown in FIG. 7, the sheath 31 includes a thin tube 31a made of aluminum material and synthetic resin tubes 31b and 31c laminated on an inner and an outer periphery of the tube 31a. In the illustration, the thickness of the peripheral walls of those tubes 31a, 31b and 31c are somewhat exaggerated. The tube 31a has a slit formed in its periphery all the way through the thickness of the peripheral wall and over an entire length of the tube 31a. Those areas of the periphery of the tube 31a in the vicinity of mating edges defined by the slit are overlapped each other. Accordingly, when the sheath 31 is bent, the mating edge portions are relatively moved in a circumferential direction of the tube 31a. The sheath 31 can be manually bent into any desired contour. By making the tube 31a from an aluminum material, a stable bent contour of the tube 31a can be maintained. This sheath 31 serves as the conventional stylet.

As best seen in FIG. 5, the sheath 31 has the attachment 32 attached to the rear end part thereof. The attachment 32 includes a base portion 32a, and a sleeve portion 32b formed forwardly of the base portion 32a. The sleeve portion 32b is fixedly inserted into the rear end part of the sheath 31. The base portion 32a of the attachment 32 is received in the receiving cavity 24 formed in the attachment 20 of the body 10. A connection sleeve 33 is threadedly engaged with the receiving portion 22 of the attachment 20. An annular flange 33a is formed on a front end of the connection sleeve 33. The annular flange 33a extends radially and inwardly of the connection sleeve 33. When the flange 33a is brought into contact with a step 32c formed between the base portion 32a and the sleeve portions 32b of the attachment 32, the attachment 32 can be detachably secured to the body 10. Thus, the rear end part of the sheath 31 can be detachably attached to the body 10.

Figure 6:
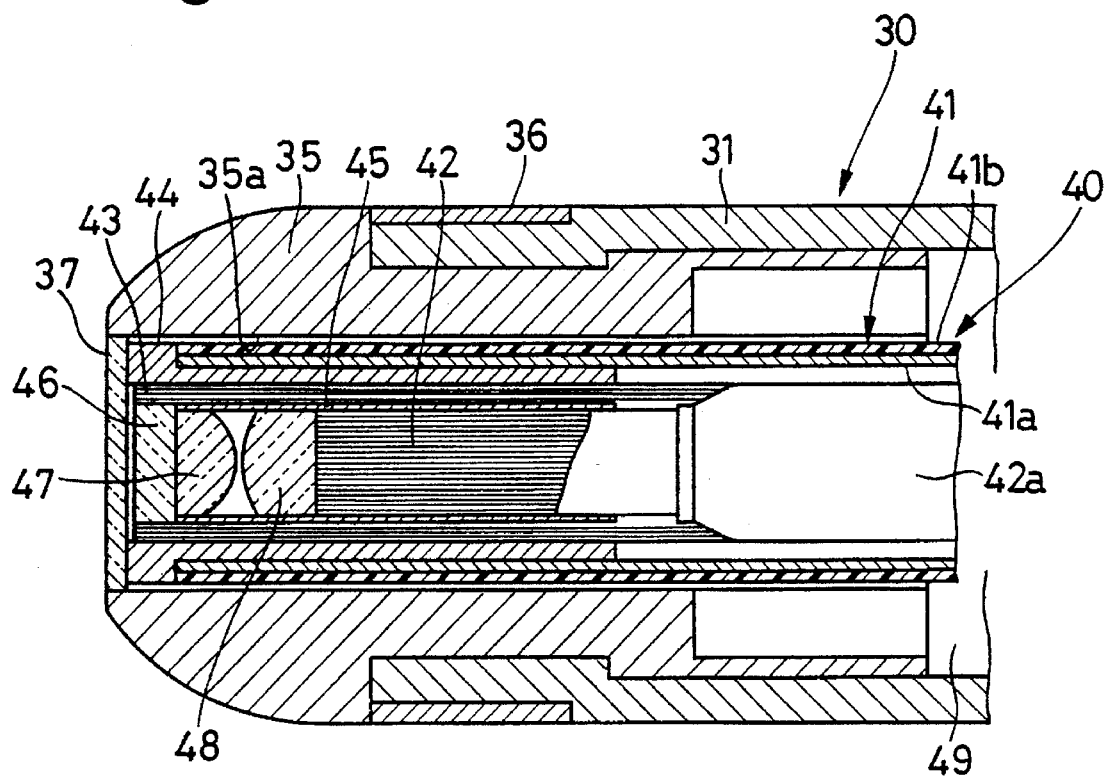
FIG. 6 is an enlarged sectional view showing a distal end part of the insert portion of the endoscope.

As best seen in FIG. 6, a chip 35 is attached to a distal end part of the sheath 31. That is, the distal end part of the sheath 31 is fixed to an outer periphery of a rear end part of the chip 35 by fixture means 36. The fixture means 36 includes an adhesive and winding. The chip 35 has a through-hole 35a extending axially. A distal open end of this through-hole 35a is closed by a glass plate 37 (transparent portion). In this way, the opening of the distal end of the sheath 31 is closed.

As best seen in FIGS. 5 and 6, the content 40 of the insert portion 30 includes a flexible cylindrical protective tube 41

(inner tube), and a bundle of optical fibers 42 for transmitting an image and a bundle of optical fibers 43 for transmitting an illumination light. The bundles of optical fibers 42 and 43 are received in the protective tube 41. An outer diameter of the protective tube 41 is smaller than an inner diameter of the sheath 31. A space 49 is formed between the protective tube 41 and the sheath 31. The protective tube 41 includes a flex 41a formed of a strip plate spirally wound and a synthetic resin tube 41b covering an outer periphery of the flex 41a. A distal end part of the protective tube 41 is fixedly secured to an outer periphery of a sleeve member 44. An auxiliary sleeve 45 is received into the sleeve member 44 through a space. A glass plate 46, convex lens 47, 48 as an objective side optical system and a distal end part of the bundle of optical fibers 42 for transmitting an image are received in the auxiliary sleeve 45 in this order rearwardly. The image transmitting bundle of optical fibers 42 are covered by a thin synthetic resin tube 42a. A distal end face of the optical fibers bundle 42 is in contact with a flat surface of the rear side convex lens 48. A distal end part of the illumination light transmitting optical fibers bundle 43 is disposed in an annular space between the sleeve member 44 and the auxiliary sleeve 45. The distal end of the bundle of optical fibers 43 is flush with front surface of the glass plate 46.

As shown in FIGS. 1, 2 and 5, a rear end part of the protective tube 41 is allowed to extend through the base portion 32a of the attachment 32 of the sheath 31 and further extend through the base portion 21 of the attachment 20 of the body 10. The rear end part of the protective tube 41 is not fixedly secured to the base portion 32a of the attachment 32 of the sheath 31 but fixedly secured only to the base portion 21 of the attachment 20 of the body 10 by adhesive or the like. The bundle of image transmitting optical fibers 42 further extend from the rear end part of the protective tube 41, extend through the body 10 and the semi-hard tube 51 and reach the eye piece portion 50. On the other hand, the bundle of illumination light transmitting optical fibers 43 further extend from the rear end part of the protective tube 41, pass through the body 10 and the light guide tube 60 and are connected to the optical connector disposed at the distal end of the light guide tube 60.

In the endoscope B, as in an ordinary endoscope, an illumination light from a light source device is made incident to the optical connector. Then, the illumination light is allowed to pass through the bundle of optical fibers 43 and output into a cavity of a patient's body (in this embodiment, airway) from the distal end of the insert portion 30. An image of the airway is made incident to the distal end face of the bundle of optical fibers 42 through the objective optical systems 47 and 48. Then, the image is allowed to pass through the bundle of optical fibers 42 and reaches the eye piece portion 50. As a consequence, the airway can be observed through the eye piece portion 50.

Next, operation of the tracheal airway thus constructed will be described in detail. The insert portion 30 of the endoscope B is preliminarily bent in accordance with the contour of the airway. At that time, since the sufficiently large space 49 is formed between the content 40 and the sheath 31, a slight deformation of the sheath 31 in section does not damage the content 40.

As shown in FIG. 1, the bent insert portion 30 is inserted into the bent insert tube structure A. Then, the second sleeve portion 2c of the attachment 2 of the insert tube structure A is inserted into the fitting sleeve portion 16 of the body 10. At that time, the second sleeve portion 2c can be easily inserted into the fitting sleeve portion 16 because the outer diameter of the rear end of the tapered surface 2x of the second sleeve portion 2c is smaller than the inner diameter of the front end of the tapered surface 16a of the fitting sleeve portion 16. Moreover, when the second sleeve portion 2c is inserted deep into the fitting sleeve portion 16, the tapered surface 2x of the second sleeve portion 2c intimately contacts the tapered surface 16a of the fitting sleeve portion 16, thus ensuring a reliable connection between the sleeve portions 2c and 16. Thus, the rear end part of the insert tube structure A is reliably attached to the body 10 of the endoscope B. In the state where the rear end part of the insert tube structure A is attached to the body 10 of the endoscope B, the distal end of the insert portion 30 of the endoscope B is generally coincident with the distal end of the insert tube structure A or slightly inwardly situated with respect to the distal end of the insert tube structure A.

The insert portion 30 of the endoscope B thus attached to the insert tube structure A is inserted into the airway from the mouth of a person (patient) who has suffered from a traffic accident or the like. Although the tube 1 of the insert tube structure A exhibits a bent contour, it cannot be smoothly inserted into the airway by itself because the tube 1 does not have a sufficiently large bending rigidity, particularly when the patient is damaged at the throat or the like. However, since the sheath 31 of the insert portion 30 is semi-hard and in addition, it has a sufficiently large bending rigidity, it is not easily deformed by resistance of the inner wall of the airway when it is inserted into the airway. Accordingly, the insert portion 30 and insert tube structure A can be inserted deep into the airway while maintaining the original bent state. Since the insert portion 30 and insert tube structure A can be inserted into the airway while observing the inner wall of the airway through the endoscope B, they can be relatively easily inserted into the airway even when the patient is damaged at the throat area as mentioned. This does not require a special technique of a well-experienced expert as in the conventional case where the insert tube portion, etc. are inserted into the airway while observing the airway by a throat mirror through the open mouth of the patient.

After the insert portion 30 and insert tube structure A are inserted deep enough into the airway, a compressed air is supplied into the balloon 3 through the fine tube 4 of the insert tube structure A. Then, the balloon 3 is inflated to contact the inner wall of the airway under pressure. By doing this, the insert tube structure A is fixedly secured to the airway. Thereafter, the insert portion 30 is withdrawn from the airway while leaving the insert tube structure A in the airway. At that time, the flange 2a of the attachment 2 of the insert tube structure A is held by one hand, and the body of the endoscope B is pulled by the other hand. Then, the press-fitting state of the second sleeve portion 2c of the attachment 2 with respect to the fitting sleeve portion 16 of the body 10 can be easily removed, and the insert portion 30 can be easily withdrawn from the insert tube structure A and airway.

Subsequently, the second sleeve portion 2c of the attachment 2 of the insert tube structure A is connected to a distal end portion of a tube of an oxygen supplying device and an oxygen is supplied into the patient's lungs through the insert tube structure A. Then, after the completion of treatment to the patient, the insert tube structure A is withdrawn from the airway.

Since the sheath 31 of the insert portion 30 of the endoscope B is changed in its bending form in accordance with each patient, it is sometimes subject to damage due to fatigue of repeated use. In such a case, only the sheath 31 can be exchanged. Specifically, in FIG. 2, the connection sleeve 33 is loosened to be removed from the receiving portion 22 of the body 10. Thereafter, when the sheath 31 is pulled, the attachment 32 of the rear end part of the sheath 31 is disengaged with the receiving cavity 24 of the body 10. As a consequence, the sheath 31 can be separated from the body 10 and the content 40 of the insert portion 30, and the separated sheath 31 can be disposed and replaced by a new sheath 31.

Other embodiments of the present invention will now be described. In those embodiments, component parts corresponding to those of the preceding embodiment are denoted by identical reference numerals and detailed description thereof is omitted. In an embodiment shown in FIG. 8, the inner peripheral surface of the second sleeve portion 2c of the attachment 2 of the insert tube structure A is formed as a tapered surface 2y, and the outer peripheral surface of the fitting sleeve portion 16 of the body 10 is formed as a tapered surface 16b. Angles of taper of the tapered surfaces 2y and 16b are equal to each other. In this embodiment, the second sleeve portion 2c of the insert tube structure A is fitted to the outer periphery of the fitting sleeve portion 16 of the body 10.

Figure 9:
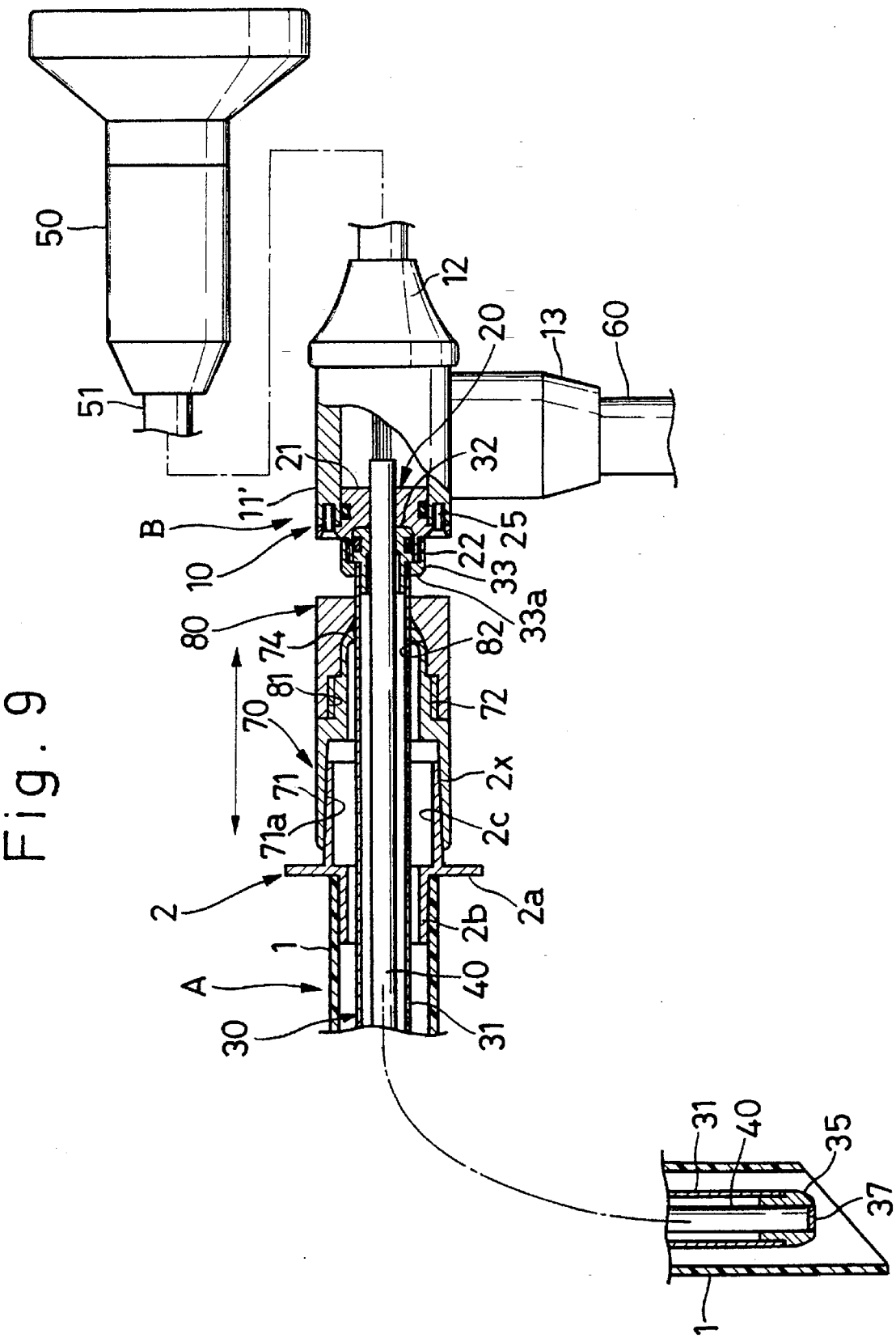
FIG. 9 is a side view, partly in section, of a tracheal airway apparatus, having a different fitting mode of the insert tube structure.
Figure 10:
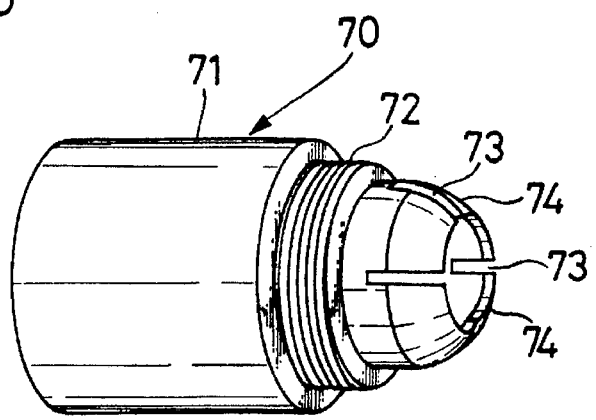
FIG. 10 is a perspective view of a fixing sleeve used in the embodiment of FIG. 9.

In an embodiment shown in FIG. 9, no fitting sleeve portion for fitting the insert tube structure A is formed on a first sleeve 11' of the body 10. The rear end part of the insert tube structure A is attached not to the body 10 of the endoscope B but to a desired position of the insert portion 30. Specifically, a slide sleeve 70 and a fixing sleeve 80 are attached to the insert portion 30 for sliding in an axial direction of the insert portion 30. A fitting sleeve portion 71 is disposed at a front part of the slide sleeve 70. The fitting sleeve portion 71 is adapted to fit the second sleeve portion 2c of the attachment 2 of the insert tube structure A. An inner peripheral surface of the fitting sleeve portion 71 is formed as a tapered surface 71a which is gradually enlarged in diameter forwardly as in the case with the first-mentioned embodiment. A threaded portion 72 is formed on an outer periphery of an intermediate portion of the slide sleeve 70. As shown in FIG. 10, a rear end part of the slide sleeve 70 is gradually reduced in diameter backwardly and its outer surface is formed as a tapered surface having four slits 73 and four elastically deformable tongue pieces 74.

On the other hand, as shown in FIG. 9, a threaded portion 81 is formed on an inner periphery of a distal end portion of the fixing sleeve 80 and a tapered surface 82, which is gradually reduced in diameter rearwardly, is formed on an inner periphery of a rear end part of the fixing sleeve portion 80. The rear end part of the slide sleeve 70 and the fixing sleeve 80 constitute fixture means for fixing the slide sleeve 70 to the insert portion 30.

With the above-mentioned construction, when the fixing sleeve 80 is screwed into the slide sleeve 70 from its rear side after the slide sleeve 70 is moved to a desired position along the insert portion 30, the tapered surface 82 of the fixing sleeve 80 causes the tongue pieces 74 of the rear end part of the slide sleeve 70 to be elastically radially inwardly deformed so that rear ends of the tongue pieces 74 contact the outer peripheral surface of the sheath 31 under pressure. By this, the slide sleeve 70 is fixedly secured to the insert portion 30. Thereafter, the second sleeve portion 2c of the attachment 2 of the insert tube structure A is fitted to the fitting sleeve portion 71 of the slide sleeve 70. This embodiment is particularly advantageous when the insert portion 30 of the endoscope B is not equal in length to the insert tube structure A. The reason is that the fitting sleeve portion 71 can be correctly positioned so that the distal end of the insert tube structure A generally coincides with the distal end of the insert portion 30 of the endoscope B as shown in FIG. 9.

Figure 11:
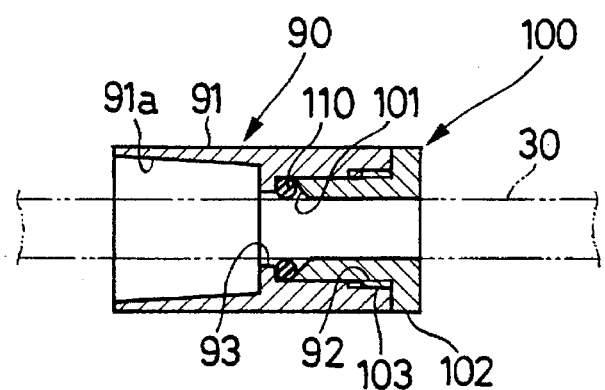
FIG. 11 is a sectional view showing a further different fitting mode of the insert tube structure.

Also in an embodiment of FIG. 11, the rear end part of the insert tube structure A is attached not to the body 10 of the endoscope B but to a desired position of the insert portion 30. Specifically, a slide sleeve 90 and a fixing sleeve 100 are attached to the insert portion 30 for sliding in an axial direction of the insert portion 30. A fitting sleeve portion 91 is disposed at a front part of the slide sleeve 90. The fitting sleeve portion 91 is adapted to fit the second sleeve portion 2c of the attachment 2 of the insert tube structure A. An inner peripheral surface of the fitting sleeve portion 91 is formed as a tapered surface 91a which is gradually enlarged in diameter forwardly as in the case with the first-mentioned embodiment. A threaded portion 92 is formed on an inner surface of a rear end part of the slide sleeve 90 and an annular engaging portion 93 extending radially inwardly is formed on an intermediate portion of the slide sleeve 90.

On the other hand, a tapered surface 101, which is gradually enlarged in diameter forwardly, is formed on an inner periphery of a front end part of the fixing sleeve 100 and a flange 102 extending radially outwardly is formed on a rear end of the fixing sleeve 100. A threaded portion 103 is formed on the outer periphery of the fixing sleeve 100 in the vicinity of the flange 102. An O-ring 110 made of a resilient material such as rubber is interposed between the engaging portion 93 of the slide sleeve 90 and the tapered surface 101 of the fixing sleeve 100.

In this embodiment, the fixture means for the slide sleeve 90 includes the fixing sleeve 100, the engaging portion 93 of the slide sleeve 90, and the O-ring 110.

With the above-mentioned construction, when the fixing sleeve 100 is screwed into the slide sleeve 90, the O-ring 110 between the tapered surface 101 of the fixing sleeve 100 and the engaging portion 93 is deformed to contact the outer periphery of the sheath 31 of the insert portion 30 under pressure. As a consequence, the slide sleeve 90 is fixedly secured to the insert portion 30, so that the fitting sleeve portion 91 is correctly positioned.

Figure 12:
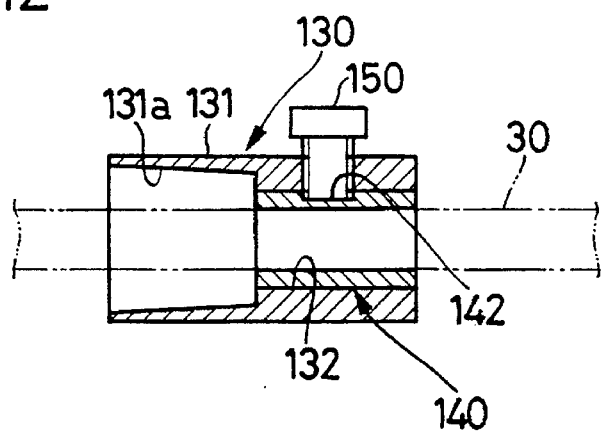
FIG. 12 is a sectional view showing a still further different fitting mode of the insert tube structure.
Figure 13:
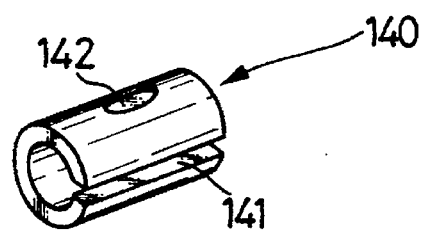
FIG. 13 is a perspective view of a fixing sleeve used in the embodiment of FIG. 12.

Also in the embodiments shown in FIGS. 12 and 13, a slide sleeve 130 and a fixing sleeve 140 are attached to the insert portion 30 for sliding in an axial direction of the insert portion 30 as in the case with the embodiments of FIGS. 9 and 10. As shown in FIG. 12, a fitting sleeve portion 131 for fitting the second sleeve portion 2c of the attachment 2 of the insert tube structure A is disposed at a front part of the slide sleeve 130. An inner peripheral surface of the fitting sleeve portion 131 is formed as a tapered surface 131a which is gradually enlarged in diameter toward a front end thereof as in the case with the first-mentioned embodiment. A rear end of the slide sleeve 130 has a receiving cavity 132 extending axially.

The fixing sleeve 140 is received in the receiving cavity 132. As shown in FIG. 13, the fixing sleeve 140 has a slit 141 formed in its periphery all the way through the thickness of the peripheral wall and over an entire length of the fixing sleeve 140. Also, a circular recess 142 is formed in the fixing sleeve 140 at an axially intermediate portion of the outer periphery and circumferentially away about 90 degrees from the slit 141.

Further, a radially piercing fixture screw 150 is screwed into a peripheral wall of the rear part of the slide sleeve 130. In a state where the distal end of the fixture screw 150 is received in the recess 142 of the fixing sleeve 140, the slide sleeve 130 and the fixing sleeve 140 are slidable together along the insert portion 30. After the completion of positioning, the fixture screw 150 is screwed further inwardly of the slide sleeve 130 to push a bottom surface of the recess 142 (outer peripheral surface of the fixing sleeve 140), so that the fixing sleeve 140 is gradually reduced in diameter to contact the outer periphery of the sheath 31 of the insert portion 30 under pressure. As a consequence, the slide sleeve 130 is fixedly secured.

In this embodiment, fixture means for fixing the slide sleeve 130 is constituted of the fixing sleeve 140 and the fixture screw 150.

Figure 8:
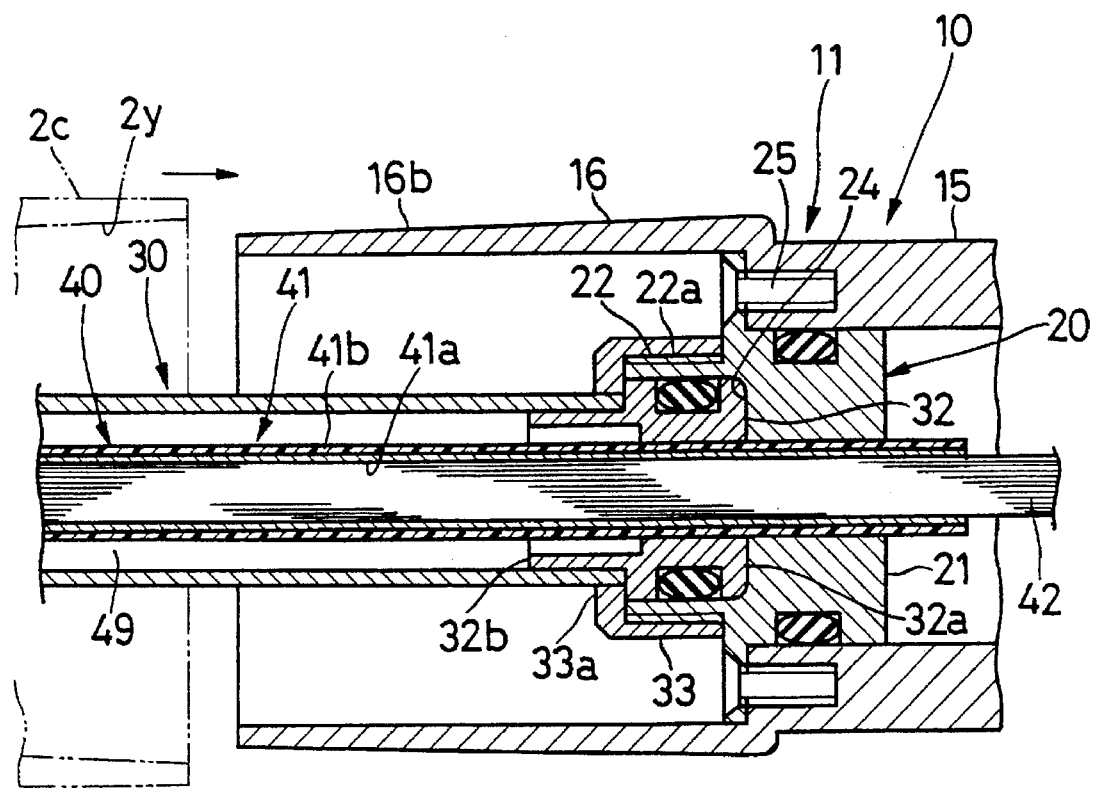
FIG. 8 is an enlarged sectional view showing another example of a front part of the body of the endoscope.

It should be noted that the present invention is not limited to the above embodiments and many changes can be made. For example, in the embodiments shown in FIGS. 9 to 13, it is possible that the outer peripheral surface of the fitting sleeve portion is formed as a tapered surface which is gradually reduced in diameter toward the front end of the fitting sleeve portion and a sleeve portion of a rear end part of the insert tube structure is attached to this outer periphery as shown in FIG. 8.

A video camera having a CCD may be connected to the eye piece portion disposed at the rear end of the body. It is also possible that in the image transmission system, a CCD is disposed rearwardly of the objective lens and signal wires connected to the CCD is guided out through the insert portion and body. In the case where the CCD is employed, a state of the airway can be displayed on the TV monitor. In this way, operators can watch the TV monitor together. This is also useful for training beginners.

It should be noted that instead of the light guide tube, an illumination device containing batteries and a lamp may be secured directly to the body. In that case, a rear end of the bundle of optical fibers is optically connected to the lamp.

It should be noted that the insert tube structure may be constituted of a tube alone.

It should be noted that the glass plate 37 disposed at the distal end of the sheath 31 may be omitted.

What is claimed is:

1. A tracheal airway apparatus comprising
   (a) a tracheal insert tube for insertion into a tracheal airway, said tracheal insert tube having a low rigidity;
   (b) an endoscope including a body portion and an insert portion extending forwardly of said body portion and inserted into said tracheal insert tube;
   (c) said insert portion of said endoscope comprising an outer tube and an inner tube received in said outer tube, said inner tube being flexible and receiving illumination light transmission means and image transmission means, said outer tube having a semi-hard property, a rear end of said outer tube being detachably attached to a distal end of said body portion of said endoscope, wherein said outer tube comprises an aluminum tube and two synthetic resin tubes laminated on an inner and an outer periphery, respectively, of said aluminum tube, said aluminum tube having a slit formed over an entire length thereof, the slit forming mating edges in said aluminum tube which overlap each other.

2. A tracheal airway apparatus according to claim 1, in which a space is formed between an outer periphery of said inner tube and an inner periphery of said outer tube.

3. A tracheal airway apparatus according to claim 2, further comprising closure means for closing an open distal end of said outer tube, said closure means having a transparent portion faced with a distal end of said inner tube.

4. A tracheal airway apparatus according to claim 3, in which said closure means has a chip fixed to the distal end part of said outer tube, said chip having a through-hole formed therein and coaxial with said outer tube, an open distal end of said through-hole being attached with a transparent plate serving as said transparent portion, the distal end part of said inner tube being received in said through-hole.

5. A tracheal airway apparatus according to claim 1, in which said body portion has a fitting sleeve portion disposed on a front end face thereof such that said fitting sleeve portion coaxially surrounds a rear end part of said insert portion, a rear end part of said tracheal insert tube being detachably fitted to said fitting sleeve portion.

6. A tracheal airway apparatus according to claim 5, in which contacting surfaces of said fitting sleeve portion and the rear part of said tracheal insert tube are tapered at a same angle of taper.

7. A tracheal airway apparatus according to claim 1, further comprising a slide sleeve axially slidably attached to said outer tube, and fixture means for fixing said slide sleeve to said outer tube at a desired position thereof, said slide sleeve having a fitting sleeve portion formed on a front part thereof, a rear end part of said tracheal insert tube being detachably fitted to said fitting sleeve portion.

8. A tracheal airway apparatus according to claim 7, in which contacting surfaces of said fitting sleeve portion and a rear end part of said insert tube are tapered at a same angle of taper.

9. A tracheal airway apparatus according to claim 1, in which a distal end of said insertion portion of said endoscope substantially coincides with a distal end of said tracheal insert tube.

10. A tracheal airway apparatus comprising:
    (a) a tracheal insert tube for insertion into a tracheal airway, said tracheal insert tube having a low rigidity;
    (b) an endoscope including a body portion and an insert portion extending forwardly of said body portion and inserted into said tracheal insert tube;
    (c) said insert portion of said endoscope comprising an outer tube and an inner tube received in said outer tube, said inner tube being flexible and receiving illumination light transmission means and image transmission means, said outer tube having a semi-hard property, a rear end of said outer tube being detachably attached to a distal end of said body portion of said endoscope, and wherein a space is formed between an outer periphery of said inner tube and an inner periphery of said outer tube; and
    (d) connection means for detachably attaching the rear end of said outer tube to the distal end of said body portion, said connection means comprising:
        (i) a cylindrical receiving portion formed on a front wall of said body portion and having a threaded portion formed on an outer periphery of said cylindrical receiving portion;
        (ii) an attachment fixed to the rear end of said outer tube and received in said cylindrical receiving portion, said inner tube being coaxial with said cylindrical receiving portion and extending rearwardly through the rear end of said outer tube, said attachment and the front wall of said body portion;
        (iii) a connection sleeve threadedly engaged with said cylindrical receiving portion, said connection sleeve having an annular flange portion formed on a distal end thereof and extending radially inwardly, said attachment being retained by said flange portion.

11. A tracheal airway apparatus comprising:
    (a) a tracheal insert tube for insertion into a tracheal airway, said tracheal insert tube having a low rigidity;

(b) an endoscope including a body portion and an insert portion extending forwardly of said body portion and inserted into said tracheal insert tube;

(c) said insert portion of said endoscope comprising an outer tube and an inner tube received in said outer tube, said inner tube being flexible and receiving illumination light transmission means and image transmission means, said outer tube having a semi-hard property, a rear end of said outer tube being detachably attached to a distal end of said body portion of said endoscope; and (d) a slide sleeve axially slidably attached to said outer tube, and fixture means for fixing said slide sleeve to said outer tube at a desired position thereof, said slide sleeve having a fitting sleeve portion formed on a front part thereof, a rear end part of said tracheal insert tube being detachably fitted to said fitting sleeve portion, wherein said fixture means includes (i) a rear end part of said slide sleeve having slits, and (ii) a fixing sleeve threadably engaged with an outer periphery of said slide sleeve and having a tapered surface on an inner periphery thereof, said tapered surface being gradually reduced in diameter rearwardly;

wherein when said fixing sleeve is threadedly engaged with said slide sleeve, the tapered surface of said fixing sleeve is brought into contact with the rear end part of said slide sleeve to cause the rear end part to be transformed radially inwardly so as to contact an outer periphery of said outer tube under pressure.

12. A tracheal airway apparatus comprising:

(a) a tracheal insert tube for insertion into a tracheal airway, said tracheal insert tube having a low rigidity;

(b) an endoscope including a body portion and an insert portion extending forwardly of said body portion and inserted into said tracheal insert tube;

(c) said insert portion of said endoscope comprising an outer tube and an inner tube received in said outer tube, said inner tube being flexible and receiving illumination light transmission means and image transmission means, said outer tube having a semi-hard property, a rear end of said outer tube being detachably attached to a distal end of said body portion of said endoscope; and (d) a slide sleeve axially slidably attached to said outer tube, and fixture means for fixing said slide sleeve to said outer tube at a desired position thereof, said slide sleeve having a fitting sleeve portion formed on a front part thereof, a rear end part of said tracheal insert tube being detachably fitted to said fitting sleeve portion, wherein said fixture means includes (i) a fixing sleeve axially slidably attached to said outer tube of said endoscope and threadedly engaged with an inner periphery of the rear part of said slide sleeve, said fixing sleeve having a tapered surface, which is gradually enlarged in diameter forwardly, formed on an inner periphery of a distal end part thereof, (ii) an annular engaging portion formed on an inner periphery of an intermediate portion in an axial direction of said slide sleeve, and (iii) an O-ring interposed between the tapered surface of the distal end part of said fixing sleeve and said engaging portion of said slide sleeve;

wherein when said fixing sleeve is screwed into said slide sleeve, said O-ring interposed between the tapered surface of the distal end part of said fixing sleeve and said engaging portion of said slide sleeve being deformed to contact the outer periphery of said outer tube under pressure.

13. A tracheal airway apparatus comprising:

(a) a tracheal insert tube for insertion into a tracheal airway, said tracheal insert tube having a low rigidity;

(b) an endoscope including a body portion and an insert portion extending forwardly of said body portion and inserted into said tracheal insert tube;

(c) said insert portion of said endoscope comprising an outer tube and an inner tube received in said outer tube, said inner tube being flexible and receiving illumination light transmission means and image transmission means, said outer tube having a semi-hard property, a rear end of said outer tube being detachably attached to a distal end of said body portion of said endoscope; and (d) a slide sleeve axially slidably attached to said outer tube, and fixture means for fixing said slide sleeve to said outer tube at a desired position thereof, said slide sleeve having a fitting sleeve portion formed on a front part thereof, a rear end part of said tracheal insert tube being detachably fitted to said fitting sleeve portion, wherein said fixture means includes (i) a fixing sleeve axially slidably attached to said outer tube of said endoscope and received in a rear part of said slide sleeve, said fixing sleeve having a slit formed therein over an entire length of said fixing sleeve, and (ii) a fixture screw which is screwed into a peripheral wall of the rear part of said slide sleeve;

wherein said fixture screw being screwed into the peripheral wall of the rear part of said slide sleeve to push the outer peripheral surface of said fixing sleeve, so that said fixing sleeve is reduced in diameter and contacts the outer periphery of said outer tube under pressure.

* * * * *